United States Patent [19]

Sugiyama

[11] Patent Number: 5,171,668

[45] Date of Patent: Dec. 15, 1992

[54] METHOD OF THE CHEMILUMINESCENCE ASSAY OF THE ACTIVITY OF PEROXIDASE

[75] Inventor: Masami Sugiyama, Tokyo, Japan

[73] Assignee: Fujirebio Inc., Tokyo, Japan

[21] Appl. No.: 413,687

[22] Filed: Sep. 29, 1989

[30] Foreign Application Priority Data

Sep. 30, 1988 [JP] Japan .................. 63-243984

[51] Int. Cl.⁵ .......................... C12Q 1/28; C12Q 1/26
[52] U.S. Cl. ...................... 435/28; 435/25; 435/968
[58] Field of Search .................... 435/28, 25

[56] References Cited

U.S. PATENT DOCUMENTS 4,729,950  3/1988  Kricka et al. ................. 435/28

FOREIGN PATENT DOCUMENTS 045220   2/1982   European Pat. Off.
124287   11/1984  European Pat. Off.
2002517  2/1979   United Kingdom.

OTHER PUBLICATIONS

Bodea et al., "Recent Advances in the Chemistry of Phenothiazines", *Advances in Heterocyclic Chemistry*, vol. 9, Academic Press, N.Y., pp. 356–368, 389–393 (1968).
Thorpe et al., Meth. Enzymol., vol. 133, Academic Press, N.Y., pp. 331–353 (1986).
Pinder et al., Meth. Enzymol., vol. XVIII, Academic Press, N.Y., pp. 24–30.
Chemical Abstracts, vol. 108, No. 21, May 23, 1988, p. 367, Abstract No. 183150O, Columbus, Ohio, U.S.: M. A. Motsenbocker: "Sensitivity Limitations Encountered in Enhanced Horseradish Peroxidase Catalyzed Chemiluminescence", & J. Biolumin. Chemilumin., 1988, 2(1), 9–16.

*Primary Examiner*—Christine M. Nucker
*Assistant Examiner*—M. P. Woodward
*Attorney, Agent, or Firm*—Oblon, Spivak, McClelland, Maier & Neustadt

[57] ABSTRACT

A method of chemiluminescence assay of the activity of peroxidase is disclosed, which employes (i) luminol or isoluminol as a substrate, (ii) hydrogen peroxide, and (iii) at lease one compound, serving as an enhancer for the activity of peroxidase, selected from the group consisting of

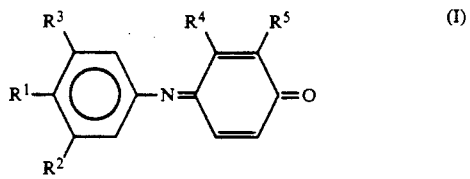

wherein $R^1$ represents a hydroxyl group, an alkali metal salt of hydroxyl group (—OM, where M is an alkali metal), an amino group which may have a substituent, a halogen, an alkyl group having 1 to 4 carbon atoms, which may have a substituent; $R^2$ and $R^3$ each represent hydrogen or a halogen; $R^4$ and $R^5$ each represent hydrogen, an alkyl group having 1 to 4 carbon atoms, which may have a substituent, or an alkoxyl group having 1 to 4 carbon atoms, which may have a substituent;

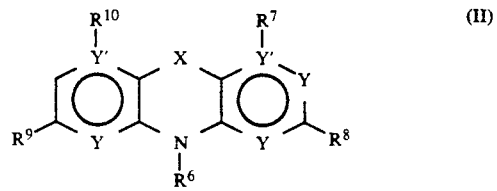

wherein $R^6$ represents an alkyl group having 1 to 6 carbon atoms, which may have a substituent, or an alkene group having 2 to 6 carbon atoms, which may have a substituent, $R^7$ to $R^{10}$ each represent hydrogen, an alkyl group having 1 to 6 carbon atoms, which may have a substituent, or a halogen, X represents oxygen or sulfur, Y represents —CH— or nitrogen, which may be the same or different, and Y' represents carbon or nitrogen, which may be the same or different.

3 Claims, 9 Drawing Sheets

METHOD OF THE PRESENT INVENTION

METHOD OF THE PRESENT INVENTION

METHOD OF THE CHEMILUMINESCENCE ASSAY OF THE ACTIVITY OF PEROXIDASE

BACKGROUND OF THE INVENTION

The present invention relates to an improved method of the chemiluminescence assay of the activity of peroxidase.

Recent research and development activities of enzyme immunoassay directed to the improvement of the sensitivity of the assay have been remarkable. Unquestionably the chemiluminescence assay is a useful means for achieving this object. For instance, it has been reported that a chemiluminescence assay using luminol has a peroxidase detection sensitivity of $10^{-16}$ mol (PNE, Nuclei Acid and Enzyme, Extra Issue No. 31, pages 51-63).

The peroxidase detection sensitivity attained by the above method is much higher than a detection sensitivity of $10^{-15}$ mol attained by a colorimetric peroxidase detection method using 2,2'-azino-di(3-ethylbenzthiazinolinesulfonate) ABTS as a substrate, and a detection sensitivity of $10^{-14}$ mol attained by a fluorescent peroxidase detection method using p-hydroxyphenyl propionic acid as a substrate.

However, the chemiluminescence assay is in fact not in general use since it has the shortcoming that the luminescent time is too short to be used in practice. Under such circumstances, a chemiluminescence assay using as p-iodophenol as an enhancer for the activity of peroxidase has been tried in an attempt to increase the detection sensitivity as reported in H. Allan, J. Microbiology Apr., 630-636, 35, 1988). This chemiluminescence assay has attained some improvement of the detection sensitivity but has the shortcoming that the reproducibility of the assay is so poor that obtained data is not always reliable.

SUMMARY OF THE INVENTION

It is therefore an object of the present invention to provide an improved method of the chemiluminescence assay of the activity of peroxidase which can attain accurate and reliable chemiluminescence assay with amplified chemiluminescence.

The object of the present invention is achieved by a method of the chemiluminescence assay of the activity of peroxidase which employs (i) luminol or isoluminol as a substrate, (ii) a hydrogen peroxide solution, and (iii) at least one compound, serving as an enhancer for the activity of peroxidase, selected from the group consisting of

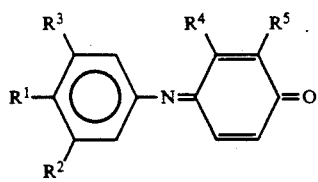

wherein $R^1$ represents a hydroxyl group, an alkali metal salt of hydroxyl group (—OM, where M is an alkali metal), an amino group which may have a substituent, a halogen, an alkyl group having 1 to 4 carbon atoms, which may have a substituent; $R^2$ and $R^3$ each represent hydrogen or a halogen; $R^4$ and $R^5$ each represent hydrogen, an alkyl group having 1 to 4 carbon atoms, which may have a substituent, or an alkoxyl group having 1 to 4 carbon atoms, which may have a substituent;

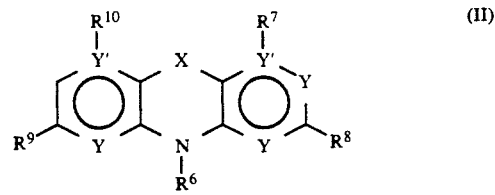

wherein $R^6$ represents an alkyl group having 1 to 6 carbon atoms, which may have a substituent, or an alkene group having 2 to 6 carbon atoms, which may have a substituent, $R^7$ to $R^{10}$ each represent hydrogen, an alkyl group having 1 to 6 carbon atoms, which may have a substituent, or a halogen, X represents oxygen or sulfur, Y represents —CH— or nitrogen, which may be the same or different, and Y' represents carbon or nitrogen, which may be the same or different.

DETAILED DESCRIPTION OF THE PREFERRED EMBODIMENTS

Figure 1:
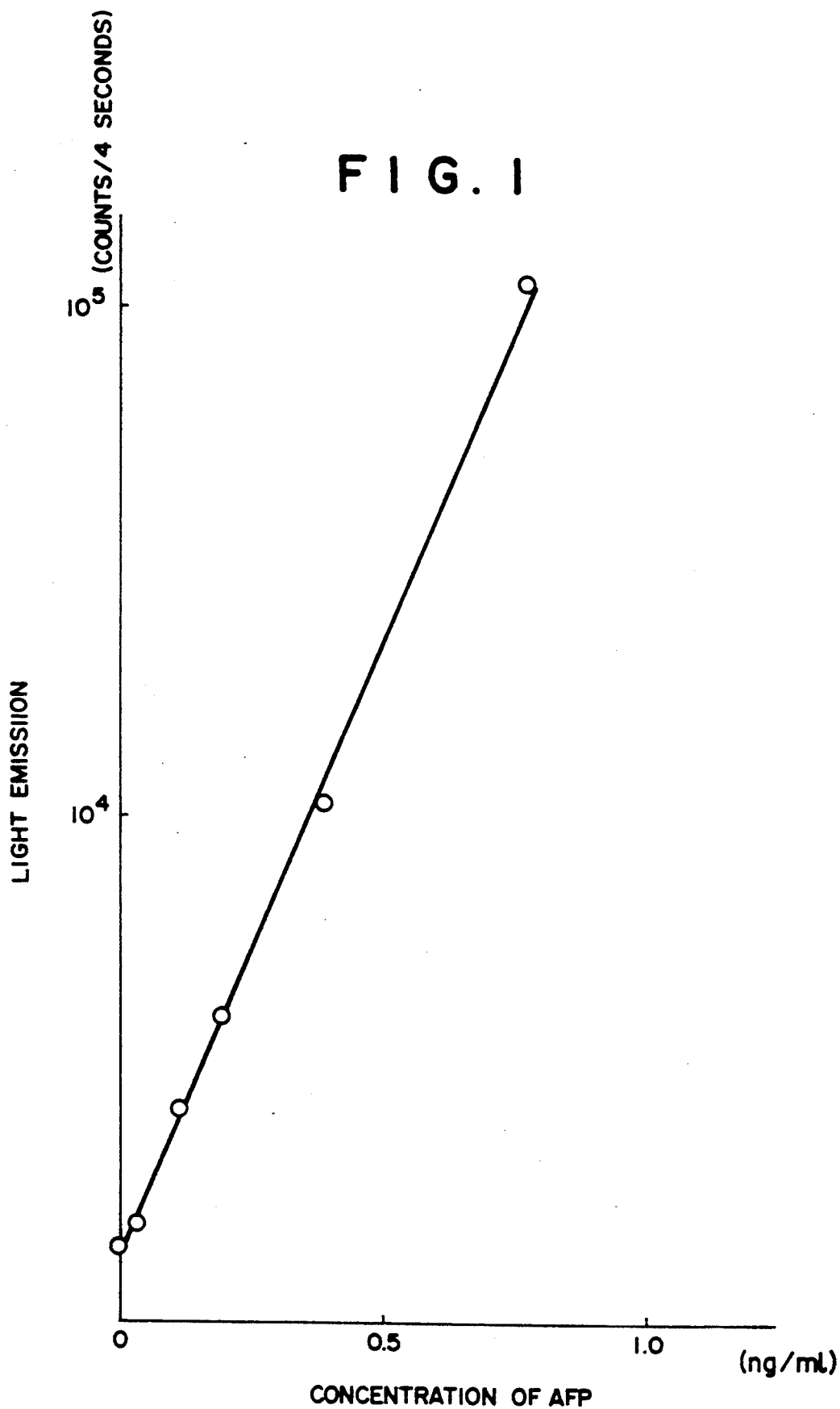
FIG. 1 shows a standard curve showing the relationship between the concentration of AFP and the light emission of a luminol substrate when a peroxidase activity enhancer comprising N-methylphenothiazine and phenolindophenol was employed.

The compounds represented by the previously mentioned formula (I) are phenolindophenol derivatives and the compounds represented by the formula (II) are phenothiazine or phenoxazine derivatives.

In formula (I), $R^1$ represents, for example, a hydroxyl group, an alkali metal salt of hydroxyl group (—OM group, where M is an alkali metal, such as sodium, potassium and calcium), an unsubstituted amino group, an amino group which has a substituent such as a monoalkyl or dialkyl group, for example, a dimethylamino group and a diethylamino group, and a diethanolamino group, a halogen such as chlorine, bromine and iodine, an alkyl group having 1 to 4 carbon atoms, which may have a substituent, such as a sodium sulfonate group, for example, sodium propane-3-sulfonate; $R^2$ and $R^3$ each, for example, represent hydrogen or a halogen such as chlorine, bromine and iodine; and $R^4$ and $R^5$ each represent, for example, hydrogen, an alkyl group having 1 to 4 carbon atoms, such as a methyl group and an ethyl group, which may have a substituent such as a sodium sulfonate group, for example, a substituted alkyl group such as sodium propane-3-sulfonate, or an alkoxyl group having 1 to 4 carbon atoms, such as a methoxy group and an ethoxy group.

Specific examples of the compounds represented by formula (I) are phenolindophenol, 2,6-dichlorophenolindophenol, 2,6-dichlorophenol-o-cresol, and phenolindoaniline.

Representative examples of the compounds of formula (II) are:

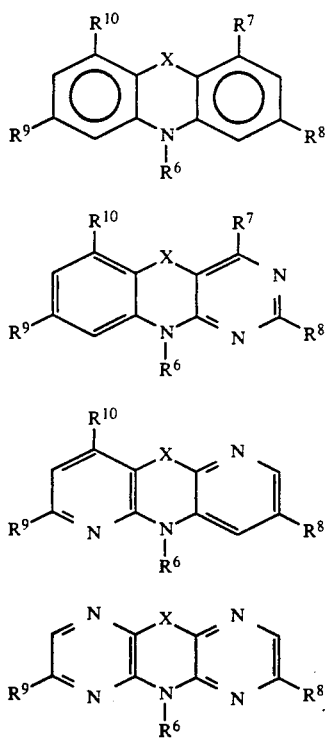

wherein $R^6$, $R^7$, $R^8$, $R^9$, and $R^{10}$, and x are respectively the same as those defined in formula (II).

Specific examples of the compounds represented by formula (II-a) are as follows:
N-methylphenoxazine,
N-ethylphenoxazine,
N-propylphenoxazine,
sodium phenoxazine-10-yl-propanesulfonate,
sodium phenoxazine-10-yl-2,4-dimethyl-1,3-butadienesulfonate,
1-methylphenoxazine-10-yl-propylsulfonate,
3-methylphenoxazine-10-yl-propylsulfonate,
6-methylphenoxazine-10-yl-propylsulfonate,
8-methylphenoxazine-10-yl-propylsulfonate,
1,3-dimethylphenoxazine-10-yl-propylsulfonate,
1,6-dimethylphenoxazine-10-yl-propylsulfonate,
1,8-dimethylphenoxazine-10-yl-propylsulfonate,
3,6-dimethylphenoxazine-10-yl-propylsulfonate,
3,8-dimethylphenoxazine-10-yl-propylsulfonate,
6,8-dimethylphenoxazine-10-yl-propylsulfonate,
1,3,6-trimethylphenoxazine-10-yl-propylsulfonate,
1,3,8-trimethylphenoxazine-10-yl-propylsulfonate,
1,6,8-trimethylphenoxazine-10-yl-propylsulfonate,
1-ethylphenoxazine-10-yl-propylsulfonate,
3-ethylphenoxazine-10-yl-propylsulfonate,
6-ethylphenoxazine-10-yl-propylsulfonate,
8-ethylphenoxazine-10-yl-propylsulfonate,
1,3-diethylphenoxazine-10-yl-propylsulfonate,
1,6-diethylphenoxazine-10-yl-propylsulfonate,
1,8-diethylphenoxazine-10-yl-propylsulfonate,
3,6-diethylphenoxazine-10-yl-propylsulfonate,
3,8-diethylphenoxazine-10-yl-propylsulfonate,
6,8-diethylphenoxazine-10-yl-propylsulfonate,
1,3,6-triethylphenoxazine-10-yl-propylsulfonate,
1,3,8-triethylphenoxazine-10-yl-propylsulfonate,
1,6,8-triethylphenoxazine-10-yl-propylsulfonate,
1-propylphenoxazine-10-yl-propylsulfonate,
3-propylphenoxazine-10-yl-propylsulfonate,
6-propylphenoxazine-10-yl-propylsulfonate,
8-propylphenoxazine-10-yl-propylsulfonate,
1,3-dipropylphenoxazine-10-yl-propylsulfonate,
1,6-dipropylphenoxazine-10-yl-propylsulfonate,
1,8-dipropylphenoxazine-10-yl-propylsulfonate,
3,6-dipropylphenoxazine-10-yl-propylsulfonate,
3,8-dipropylphenoxazine-10-yl-propylsulfonate,
6,8-dipropylphenoxazine-10-yl-propylsulfonate,
1,3,6-tripropylphenoxazine-10-yl-propylsulfonate,
1,3,8-tripropylphenoxazine-10-yl-propylsulfonate,
1,6,8-tripropylphenoxazine-10-yl-propylsulfonate,
1-butylphenoxazine-10-yl-propylsulfonate,
3-butylphenoxazine-10-yl-propylsulfonate,
6-butylphenoxazine-10-yl-propylsulfonate,
8-butylphenoxazine-10-yl-propylsulfonate,
1,3-dibutylphenoxazine-10-yl-propylsulfonate,
1,6-dibutylphenoxazine-10-yl-propylsulfonate,
1,8-dibutylphenoxazine-10-yl-propylsulfonate,
3,6-dibutylphenoxazine-10-yl-propylsulfonate,
3,8-dibutylphenoxazine-10-yl-propylsulfonate,
6,8-dibutylphenoxazine-10-yl-propylsulfonate,
1,3,6-tributylphenoxazine-10-yl-propylsulfonate,
1,3,8-tributylphenoxazine-10-yl-propylsulfonate,
1,6,8-tributylphenoxazine-10-yl-propylsulfonate,
1-chlorophenoxazine-10-yl-propylsulfonate,
3-chlorophenoxazine-10-yl-propylsulfonate,
6-chlorophenoxazine-10-yl-propylsulfonate,
8-chlorophenoxazine-10-yl-propylsulfonate,
1-bromophenoxazine-10-yl-propylsulfonate,
3-bromophenoxazine-10-yl-propylsulfonate,
6-bromophenoxazine-10-yl-propylsulfonate,
8-bromophenoxazine-10-yl-propylsulfonate,
N-methylphenothiazine,
N-ethylphenothiazine,
N-propylphenothiazine,
sodium phenothiazine-10-yl-propanesulfonate,
sodium phenothiazine-10-yl-2,4-dimethyl-1,3-butadienesulfonate,
1-methylphenothiazine-10-yl-propylsulfonate,
3-methylphenothiazine-10-yl-propylsulfonate,
6-methylphenothiazine-10-yl-propylsulfonate, 8-methylphenothiazine-10-yl-propylsulfonate,
1,3-dimethylphenothiazine-10-yl-propylsulfonate,
1,6-dimethylphenothiazine-10-yl-propylsulfonate,
1,8-dimethylphenothiazine-10-yl-propylsulfonate,
3,6-dimethylphenothiazine-10-yl-propylsulfonate,
3,8-dimethylphenothiazine-10-yl-propylsulfonate,
6,8-dimethylphenothiazine-10-yl-propylsulfonate,
1,3,6-trimethylphenothiazine-10-yl-propylsulfonate,
1,3,8-trimethylphenothiazine-10-yl-propylsulfonate,
1,6,8-trimethylphenothiazine-10-yl-propylsulfonate,
1-ethylphenothiazine-10-yl-propylsulfonate,
3-ethylphenothiazine-10-yl-propylsulfonate,
6-ethylphenothiazine-10-yl-propylsulfonate,
8-ethylphenothiazine-10-yl-propylsulfonate,
1,3-diethylphenothiazine-10-yl-propylsulfonate,
1,6-diethylphenothiazine-10-yl-propylsulfonate,
1,8-diethylphenothiazine-10-yl-propylsulfonate,
3,6-diethylphenothiazine-10-yl-propylsulfonate,
3,8-diethylphenothiazine-10-yl-propylsulfonate,
6,8-diethylphenothiazine-10-yl-propylsulfonate,
1,3,6-triethylphenothiazine-10-yl-propylsulfonate,
1,3,8-triethylphenothiazine-10-yl-propylsulfonate,
1,6,8-triethylphenothiazine-10-yl-propylsulfonate,
1-propylphenothiazine-10-yl-propylsulfonate,
3-propylphenothiazine-10-yl-propylsulfonate,
6-propylphenothiazine-10-yl-propylsulfonate,
8-propylphenothiazine-10-yl-propylsulfonate,
1,3-dipropylphenothiazine-10-yl-propylsulfonate,
1,6-dipropylphenothiazine-10-yl-propylsulfonate,
1,8-dipropylphenothiazine-10-yl-propylsulfonate,
3,6-dipropylphenothiazine-10-yl-propylsulfonate,
3,8-dipropylphenothiazine-10-yl-propylsulfonate,
6,8-dipropylphenothiazine-10-yl-propylsulfonate,
1,3,6-tripropylphenothiazine-10-yl-propylsulfonate,
1,3,8-tripropylphenothiazine-10-yl-propylsulfonate,
1,6,8-tripropylphenothiazine-10-yl-propylsulfonate,
1-butylphenothiazine-10-yl-propylsulfonate,
3-butylphenothiazine-10-yl-propylsulfonate,
6-butylphenothiazine-10-yl-propylsulfonate,
8-butylphenothiazine-10-yl-propylsulfonate,
1,3-dibutylphenothiazine-10-yl-propylsulfonate,
1,6-dibutylphenothiazine-10-yl-propylsulfonate,
1,8-dibutylphenothiazine-10-yl-propylsulfonate,
3,6-dibutylphenothiazine-10-yl-propylsulfonate,
3,8-dibutylphenothiazine-10-yl-propylsulfonate,
6,8-dibutylphenothiazine-10-yl-propylsulfonate,
1,3,6-tributylphenothiazine-10-yl-propylsulfonate,
1,3,8-tributylphenothiazine-10-yl-propylsulfonate,
1,6,8-tributylphenothiazine-10-yl-propylsulfonate,
1-chlorophenothiazine-10-yl-propylsulfonate,
3-chlorophenothiazine-10-yl-propylsulfonate,
6-chlorophenothiazine-10-yl-propylsulfonate,
8-chlorophenothiazine-10-yl-propylsulfonate,
1-bromophenothiazine-10-yl-propylsulfonate,
3-bromophenothiazine-10-yl-propylsulfonate,
6-bromophenothiazine-10-yl-propylsulfonate, and
8-bromophenothiazine-10-yl-propylsulfonate.

Specific examples of the compounds represented by formula (II-b) are as follows:
N-methylpyrimidylphenoxazine,
N-ethylpyrimidylphenoxazine,
N-propylpyrimidylphenoxazine,
sodium pyrimidylphenoxazine-10-yl-propanesulfonate,
sodium pyrimidylphenoxazine-10-yl-2,4-dimethyl-1,3-butadienesulfonate,
1-methylpyrimidylphenoxazine-10-yl-propylsulfonate,
3-methylpyrimidylphenoxazine-10-yl-propylsulfonate,
6-methylpyrimidylphenoxazine-10-yl-propylsulfonate,
8-methylpyrimidylphenoxazine-10-yl-propylsulfonate,
1,3-dimethylpyrimidylphenoxazine-10-yl-propylsulfonate,
1,6-dimethylpyrimidylphenoxazine-10-yl-propylsulfonate,
1,8-dimethylpyrimidylphenoxazine-10-yl-propylsulfonate,
3,6-dimethylpyrimidylphenoxazine-10-yl-propylsulfonate,
3,8-dimethylpyrimidylphenoxazine-10-yl-propylsulfonate,
6,8-dimethylpyrimidylphenoxazine-10-yl-propylsulfonate,
1,3,6-trimethylpyrimidylphenoxazine-10-yl-propylsulfonate,
1,3,8-trimethylpyrimidylphenoxazine-10-yl-propylsulfonate,
1,6,8-trimethylpyrimidylphenoxazine-10-yl-propylsulfonate,
1-ethylpyrimidylphenoxazine-10-yl-propylsulfonate,
3-ethylpyrimidylphenoxazine-10-yl-propylsulfonate,
6-ethylpyrimidylphenoxazine-10-yl-propylsulfonate,
8-ethylpyrimidylphenoxazine-10-yl-propylsulfonate,
1,3-diethylpyrimidylphenoxazine-10-yl-propylsulfonate,
1,6-diethylpyrimidylphenoxazine-10-yl-propylsulfonate,
1,8-diethylpyrimidylphenoxazine-10-yl-propylsulfonate,
3,6-diethylpyrimidylphenoxazine-10-yl-propylsulfonate,
3,8-diethylpyrimidylphenoxazine-10-yl-propylsulfonate,
6,8-diethylpyrimidylphenoxazine-10-yl-propylsulfonate,
1,3,6-triethylpyrimidylphenoxazine-10-yl-propylsulfonate,
1,3,8-triethylpyrimidylphenoxazine-10-yl-propylsulfonate,
1,6,8-triethylpyrimidylphenoxazine-10-yl-propylsulfonate,
1-propylpyrimidylphenoxazine-10-yl-propylsulfonate,
3-propylpyrimidylphenoxazine-10-yl-propylsulfonate,
6-propylpyrimidylphenoxazine-10-yl-propylsulfonate,
8-propylpyrimidylphenoxazine-10-yl-propylsulfonate,
1,3-dipropylpyrimidylphenoxazine-10-yl-propylsulfonate,
1,6-dipropylpyrimidylphenoxazine-10-yl-propylsulfonate,
1,8-dipropylpyrimidylphenoxazine-10-yl-propylsulfonate,
3,6-dipropylpyrimidylphenoxazine-10-yl-propylsulfonate,
3,8-dipropylpyrimidylphenoxazine-10-yl-propylsulfonate,
6,8-dipropylpyrimidylphenoxazine-10-yl-propylsulfonate,
1,3,6-tripropylpyrimidylphenoxazine-10-yl-propylsulfonate,
1,3,8-tripropylpyrimidylphenoxazine-10-yl-propylsulfonate,
1,6,8-tripropylpyrimidylphenoxazine-10-yl-propylsulfonate,
1-butylpyrimidylphenoxazine-10-yl-propylsulfonate,
3-butylpyrimidylphenoxazine-10-yl-propylsulfonate,
6-butylpyrimidylphenoxazine-10-yl-propylsulfonate,
8-butylpyrimidylphenoxazine-10-yl-propylsulfonate, 1,3-dibutylpyrimidylphenoxazine-10-yl-propylsulfonate,
1,6-dibutylpyrimidylphenoxazine-10-yl-propylsulfonate,
1,8-dibutylpyrimidylphenoxazine-10-yl-propylsulfonate,
3,6-dibutylpyrimidylphenoxazine-10-yl-propylsulfonate,
3,8-dibutylpyrimidylphenoxazine-10-yl-propylsulfonate,
6,8-dibutylpyrimidylphenoxazine-10-yl-propylsulfonate,
1,3,6-tributylpyrimidylphenoxazine-10-yl-propylsulfonate,
1,3,8-tributylpyrimidylphenoxazine-10-yl-propylsulfonate,
1,6,8-tributylpyrimidylphenoxazine-10-yl-propylsulfonate,
1-chloropyrimidylphenoxazine-10-yl-propylsulfonate,
3-chloropyrimidylphenoxazine-10-yl-propylsulfonate,
6-chloropyrimidylphenoxazine-10-yl-propylsulfonate,
8-chloropyrimidylphenoxazine-10-yl-propylsulfonate,
1-bromopyrimidylphenoxazine-10-yl-propylsulfonate,
3-bromopyrimidylphenoxazine-10-yl-propylsulfonate,
6-bromopyrimidylphenoxazine-10-yl-propylsulfonate,
8-bromopyrimidylphenoxazine-10-yl-propylsulfonate,
N-methylpyrimidylphenothiazine,
N-ethylpyrimidylphenothiazine,
N-propylpyrimidylphenothiazine,
sodium pyrimidylphenothiazine-10-yl-propanesulfonate,
sodium pyrimidylphenothiazine-10-yl-2,4-dimethyl-1,3-butadienesulfonate,
1-methylpyrimidylphenothiazine-10-yl-propylsulfonate,
3-methylpyrimidylphenothiazine-10-yl-propylsulfonate,
6-methylpyrimidylphenothiazine-10-yl-propylsulfonate,
8-methylpyrimidylphenothiazine-10-yl-propylsulfonate,
1,3-dimethylpyrimidylphenothiazine-10-yl-propylsulfonate,
1,6-dimethylpyrimidylphenothiazine-10-yl-propylsulfonate,
1,8-dimethylpyrimidylphenothiazine-10-yl-propylsulfonate,
3,6-dimethylpyrimidylphenothiazine-10-yl-propylsulfonate,
3,8-dimethylpyrimidylphenothiazine-10-yl-propylsulfonate,
6,8-dimethylpyrimidylphenothiazine-10-yl-propylsulfonate,
1,3,6-trimethylpyrimidylphenothiazine-10-yl-propylsulfonate,
1,3,8-trimethylpyrimidylphenothiazine-10-yl-propylsulfonate,
1,6,8-trimethylpyrimidylphenothiazine-10-yl-propylsulfonate,
1-ethylpyrimidylphenothiazine-10-yl-propylsulfonate,
3-ethylpyrimidylphenothiazine-10-yl-propylsulfonate,
6-ethylpyrimidylphenothiazine-10-yl-propylsulfonate,
8-ethylpyrimidylphenothiazine-10-yl-propylsulfonate,
1,3-diethylpyrimidylphenothiazine-10-yl-propylsulfonate,
1,6-diethylpyrimidylphenothiazine-10-yl-propylsulfonate,
1,8-diethylpyrimidylphenothiazine-10-yl-propylsulfonate,
3,6-diethylpyrimidylphenothiazine-10-yl-propylsulfonate,
3,8-diethylpyrimidylphenothiazine-10-yl-propylsulfonate,
6,8-diethylpyrimidylphenothiazine-10-yl-propylsulfonate,
1,3,6-triethylpyrimidylphenothiazine-10-yl-propylsulfonate,
1,3,8-triethylpyrimidylphenothiazine-10-yl-propylsulfonate,
1,6,8-triethylpyrimidylphenothiazine-10-yl-propylsulfonate,
1-propylpyrimidylphenothiazine-10-yl-propylsulfonate,
3-propylpyrimidylphenothiazine-10-yl-propylsulfonate,
6-propylpyrimidylphenothiazine-10-yl-propylsulfonate,
8-propylpyrimidylphenothiazine-10-yl-propylsulfonate,
1,3-dipropylpyrimidylphenothiazine-10-yl-propylsulfonate,
1,6-dipropylpyrimidylphenothiazine-10-yl-propylsulfonate,
1,8-dipropylpyrimidylphenothiazine-10-yl-propylsulfonate,
3,6-dipropylpyrimidylphenothiazine-10-yl-propylsulfonate,
3,8-dipropylpyrimidylphenothiazine-10-yl-propylsulfonate,
6,8-dipropylpyrimidylphenothiazine-10-yl-propylsulfonate,
1,3,6-tripropylpyrimidylphenothiazine-10-yl-propylsulfonate,
1,3,8-tripropylpyrimidylphenothiazine-10-yl-propylsulfonate,
1,6,8-tripropylpyrimidylphenothiazine-10-yl-propylsulfonate,
1-butylpyrimidylphenothiazine-10-yl-propylsulfonate,
3-butylpyrimidylphenothiazine-10-yl-propylsulfonate,
6-butylpyrimidylphenothiazine-10-yl-propylsulfonate,
8-butylpyrimidylphenothiazine-10-yl-propylsulfonate,
1,3-dibutylpyrimidylphenothiazine-10-yl-propylsulfonate,
1,6-dibutylpyrimidylphenothiazine-10-yl-propylsulfonate,
1,8-dibutylpyrimidylphenothiazine-10-yl-propylsulfonate,
3,6-dibutylpyrimidylphenothiazine-10-yl-propylsulfonate,
3,8-dibutylpyrimidylphenothiazine-10-yl-propylsulfonate,
6,8-dibutylpyrimidylphenothiazine-10-yl-propylsulfonate,
1,3,6-tributylpyrimidylphenothiazine-10-yl-propylsulfonate,
1,3,8-tributylpyrimidylphenothiazine-10-yl-propylsulfonate,
1,6,8-tributylpyrimidylphenothiazine-10-yl-propylsulfonate,
1-chloropyrimidylphenothiazine-10-yl-propylsulfonate,
3-chloropyrimdiylphenothiazine-10-yl-propylsulfonate,
6-chloropyrimidylphenothiazine-10-yl-propylsulfonate,
8-chloropyrimidylphenothiazine-10-yl-propylsulfonate,
1-bromopyrimidylphenothiazine-10-yl-propylsulfonate,
3-bromopyrimidylphenothiazine-10-yl-propylsulfonate,
6-bromopyrimidylphenothiazine-10-yl-propylsulfonate,
and
8-bromopyrimidylphenothiazine-10-yl-propylsulfonate.

Specific examples of the compounds represented by formula (II-c) are as follows:
N-methylpyridylphenoxazine,
N-ethylpyridylphenoxazine,
N-propylpyridylphenoxazine,
sodium pyridylphenoxazine-10-yl-propanesulfonate,
sodium pyridylphenoxazine-10-yl-2,4-dimethyl-1,3-butadienesulfonate,
3-methylpyridylphenoxazine-10-yl-propylsulfonate,
6-methylpyridylphenoxazine-10-yl-propylsulfonate,
8-methylpyridylphenoxazine-10-yl-propylsulfonate,
3,6-dimethylpyridylphenoxazine-10-yl-propylsulfonate,
3,8-dimethylpyridylphenoxazine-10-yl-propylsulfonate,
6,8-dimethylpyridylphenoxazine-10-yl-propylsulfonate,
3-ethylpyridylphenoxazine-10-yl-propylsulfonate,
6-ethylpyridylphenoxazine-10-yl-propylsulfonate,
8-ethylpyridylphenoxazine-10-yl-propylsulfonate,
3,6-diethylpyridylphenoxazine-10-yl-propylsulfonate,
3,8-diethylpyridylphenoxazine-10-yl-propylsulfonate,
6,8-diethylpyridylphenoxazine-10-yl-propylsulfonate,
3-propylpyridylphenoxazine-10-yl-propylsulfonate,
6-propylpyridylphenoxazine-10-yl-propylsulfonate,
8-propylpyridylphenoxazine-10-yl-propylsulfonate,
3,6-dipropylpyridylphenoxazine-10-yl-propylsulfonate,
3,8-dipropylpyridylphenoxazine-10-yl-propylsulfonate,
6,8-dipropylpyridylphenoxazine-10-yl-propylsulfonate,
3-butylpyridylphenoxazine-10-yl-propylsulfonate,
6-butylpyridylphenoxazine-10-yl-propylsulfonate,
8-butylpyridylphenoxazine-10-yl-propylsulfonate,
3,6-dibutylpyridylphenoxazine-10-yl-propylsulfonate,
3,8-dibutylpyridylphenoxazine-10-yl-propylsulfonate,
6,8-dibutylpyridylphenoxazine-10-yl-propylsulfonate,
3-chloropyridylphenoxazine-10-yl-propylsulfonate,
6-chloropyridylphenoxazine-10-yl-propylsulfonate,
8-chloropyridylphenoxazine-10-yl-propylsulfonate,
3-bromopyridylphenoxazine-10-yl-propylsulfonate,
6-bromopyridylphenoxazine-10-yl-propylsulfonate,
8-bromopyridylphenoxazine-10-yl-propylsulfonate,
N-methylpyridylphenothiazine,
N-ethylpyridylphenothiazine,
N-propylpyridylphenothiazine,
sodium pyridylphenothiazine-10-yl-propanesulfonate,
sodium pyridylphenothiazine-10-yl-2,4-dimethyl-1,3-butadienesulfonate,
3-methylpyridylphenothiazine-10-yl-propylsulfonate,
6-methylpyridylphenothiazine-10-yl-propylsulfonate,
8-methylpyridylphenothiazine-10-yl-propylsulfonate,
3,6-dimethylpyridylphenothiazine-10-yl-propylsulfonate,
3,8-dimethylpyridylphenothiazine-10-yl-propylsulfonate,
6,8-dimethylpyridylphenothiazine-10-yl-propylsulfonate,
3-ethylpyridylphenothiazine-10-yl-propylsulfonate,
6-ethylpyridylphenothiazine-10-yl-propylsulfonate,
8-ethylpyridylphenothiazine-10-yl-propylsulfonate,
3,6-diethylpyridylphenothiazine-10-yl-propylsulfonate,
3,8-diethylpyridylphenothiazine-10-yl-propylsulfonate,
6,8-diethylpyridylphenothiazine-10-yl-propylsulfonate,
3-propylpyridylphenothiazine-10-yl-propylsulfonate,
6-propylpyridylphenothiazine-10-yl-propylsulfonate,
8-propylpyridylphenothiazine-10-yl-propylsulfonate,
3,6-dipropylpyridylphenothiazine-10-yl-propylsulfonate,
3,8-dipropylpyridylphenothiazine-10-yl-propylsulfonate,
6,8-dipropylpyridylphenothiazine-10-yl-propylsulfonate,
3-butylpyridylphenothiazine-10-yl-propylsulfonate,
6-butylpyridylphenothiazine-10-yl-propylsulfonate,
8-butylpyridylphenothiazine-10-yl-propylsulfonate,
3,6-dibutylpyridylphenothiazine-10-yl-propylsulfonate,
3,8-dibutylpyridylphenothiazine-10-yl-propylsulfonate,
6,8-dibutylpyridylphenothiazine-10-yl-propylsulfonate,
3-chloropyridylphenothiazine-10-yl-propylsulfonate,
6-chloropyridylphenothiazine-10-yl-propylsulfonate,
8-chloropyridylphenothiazine-10-yl-propylsulfonate,
3-bromopyridylphenothiazine-10-yl-propylsulfonate,
6-bromopyridylphenothiazine-10-yl-propylsulfonate,
and
8-bromopyridylphenothiazine-10-yl-propylsulfonate.

Specific examples of the compounds represented by formula (II-d) are as follows:
N-methyldipyrazinophenoxazine,
N-ethyldipyrazinophenoxazine,
N-propyldipyrazinophenoxazine,
sodium dipyrazinophenoxazine-10-yl-propanesulfonate,
sodium dipyrazinophenoxazine-10-yl-2,4-dimethyl-1,3-butadienesulfonate,
3-methyldipyrazinophenoxazine-10-yl-propylsulfonate,
6-methyldipyrazinophenoxazine-10-yl-propylsulfonate,
3,6-dimethyldipyrazinophenoxazine-10-yl-propylsulfonate,
3-ethyldipyrazinophenoxazine-10-yl-propylsulfonate,
6-ethyldipyrazinophenoxazine-10-yl-propylsulfonate,
3,6-diethyldipyrazinophenoxazine-10-yl-propylsulfonate,
3-propyldipyrazinophenoxazine-10-yl-propylsulfonate,
6-propyldipyrazinophenoxazine-10-yl-propylsulfonate,
3,6-dipropyldipyrazinophenoxazine-10-yl-propylsulfonate,
3-butyldipyrazinophenoxazine-10-yl-propylsulfonate,
6-butyldipyrazinophenoxazine-10-yl-propylsulfonate,
3,6-dibutyldipyrazinophenoxazine-10-yl-propylsulfonate,
3-chlorodiyrazinophenoxazine-10-yl-propylsulfonate,
6-chlorodipyrazinophenoxazine-10-yl-propylsulfonate,
3-bromodipyrazinophenoxazine-10-yl-propylsulfonate,
6-bromodipyrazinophenoxazine-10-yl-propylsulfonate,
N-methyldipyrazinophenothiazine,
N-ethyldipyrazinophenothiazine,
N-propyldipyrazinophenothiazine,
sodium dipyrazinophenothiazine-10-yl-propanesulfonate,
sodium dipyrazinophenothiazine-10-yl-2,4-dimethyl-1,3-butadienesulfonate,
3-methyldipyrazinophenothiazine-10-yl-propylsulfonate,
6-methyldipyrazinophenothiazine-10-yl-propylsulfonate,
3,6-dimethyldipyrazinophenothiazine-10-yl-propylsulfonate,
3-ethyldipyrazinophenothiazine-10-yl-propylsulfonate,
6-ethyldipyrazionphenothiazine-10-yl-propylsulfonate,
3,6-diethyldipyrazinophenothiazine-10-yl-propylsulfonate,
3-propyldipyrazinophenothiazine-10-yl-propylsulfonate,
6-propyldipyrazinophenothiazine-10-yl-propylsulfonate,
3,6-dipropyldipyrazinophenothiazine-10-yl-propylsulfonate,
3-butyldipyrazinophenothiazine-10-yl-propylsulfonate,
6-butyldipyrazinophenothiazine-10-yl-propylsulfonate,
3,6-dibutyldipyrazinophenothiazine-10-yl-propylsulfonate, 3-chlorodipyrazinophenothiazine-10-yl-propylsulfonate,
6-chlorodipyrazinophenothiazine-10-yl-propylsulfonate,
3-bromodipyrazinophenothiazine-10-yl-propylsulfonate, and
6-bromodipyrazinophenothiazine-10-yl-propylsulfonate.

In the present invention, an antigen-antibody reaction is carried out. More specifically, for example, an antigen is allowed to react with a peroxidase-labelled antibody to form an antigen-antibody complex. The thus formed antigen-antibody complex is then allowed to react with a fixed antibody, so that the activity of the peroxidase is measured by the chemiluminescence which is generated by the reaction between luminol or isoluminol serving as a substrate in the presence of hydrogen peroxide. Furthermore, in the present invention, the chemiluminescence is enhanced for accurate and reliable measurement by addition of at least one compound selected from the group consisting of the compounds of formula (I) and the compounds of formula (II) to the above chemiluminescent system.

Peroxidase, luminol and isoluminol for use in the present invention are commercially available.

In practice, in order to efficiently enhance the emission of light of the substrate, the compounds of formula (I) and the compounds of formula (II) are employed, preferably with a concentration of 5 to 300 μM, more preferably with a concentration of 10 to 200 μM.

The measurement of the light emission can be carried out after the previously mentioned antigen-antibody reaction by using luminol or isoluminol with a concentration of 50 to 1000 μM, preferably with a concentration of 200 to 300 μM, and a hydrogen peroxide solution with a concentration of 100 to 1000 μM, in a buffer solution, for example, a tricine-NaOH buffer solution with pH 8 to pH 8.5.

It is preferable that the compounds of formula (I) and the compounds of formula (II) be added immediately after the addition of the above-mentioned substrate. At that moment, the temperature of the buffer solution is in the range of 20° C. to 40° C., preferably in the range of 25° C. to 37° C.

The measurement of light emission is generally carried out by placing in a photoncounter a container containing measurement reagents therein, for instance, a test tube. However, in the case where the measurement is carried out by using a solid phase material, for instance, polystyrene beads, the beads are washed and taken out, and the measurement can be carried out in a fresh test tube.

The subjects for the measurement by the method of the chemiluminescence assay of the activity of peroxidase according to the present invention are, for example, proteins such as AFP, insulin and Ferritin, varieties of carcinomatous antigens such as carcinoembryonic antigen (CEA), antigens such HBs, varieties of hormones such as thyroid stimulating hormone (TSH), and antibodies such as IgG and IgM.

The compounds of formula (I) and the compounds of formula (II) have the function of enhancing with extremely high efficiency the reaction of (i) luminol or isoluminol and (ii) hydrogen peroxide in the assay of the activity of peroxidase and therefore can be applied to the chemiluminescent EIA.

The present invention will now be explained in more detail by referring the following reference examples and examples of the present invention;

Reference Example 1

[Preparation of peroxidase-labelled α-fetoprotein (AFP antibody)]

An AFP antibody was obtained from a mouse and subjected to pepsin digestion, so that F(ab')2 was obtained in accordance with a conventional method as described in "Enzyme Immuno Assay" 3rd Edition, page 86-, published by Igaku-shoin Co., Ltd.

1 ml of the thus obtained AFP antibody was dialyzed against a 0.1M phosphate buffer solution (pH=6.3, containing 1 mM EDTA). 50 μl of 0.2M 2-mercaptoethylamine was added to the dialyzed AFP antibody and the mixture was then allowed to stand at 37° C. for 3 hours, followed by desalting by use of G-25, whereby Fab' was obtained.

To a peroxidase solution with a concentration of 20 mg/ml, dissolved in a 0.1M phosphonate buffer solution (pH=7.0), there was added a dimethlformamide (DMF) solution of succimidyl-4-(N-maleinimidomethyl)cyclohexane-1-carboxylate (SMCC)(10 mg/150 μl, and the mixture was allowed to react with stirring at 30° C.

The reaction mixture was then centrifuged so that a precipitate formed therein was removed therefrom. The reaction mixture was desalted by use of G-25 in the same manner as mentioned above.

The previously obtained Fab' and the MMC peroxidase was mixed in a molar ratio of 1:2 and then allowed to react at 4° C. for 24 hours, followed by purifying the reaction product with gel chromatography, whereby a peroxidase-labelled AFP antibody was obtained.

Reference Example 2

[Preparation of reagents for the assay of peroxidase activity]

(a) Dimethyl sulfoxide (DMSO) solutions of N,N-dimethylindoaniline, 2,6-dichlorophenolindo-o-cresol, phenolindophenol, N-methylphenothiazine, and a combination of phenolindophenol and N-methylphenathiazine, serving as peroxidase activity enhancers, with the addition of a tricine-NaOH buffer solution (pH=8.4, 50 mM) containing 0.02% Pelex OT-P (made by Kao Atlas Co., Ltd.), were prepared in such a fashion that their initial concentrations thereof were 1 μM to 100 μM, whereby five reagents for the assay of peroxidase activity were prepared as listed in Table 1.

(b) A substrate solution of luminol was prepared by dissolving luminol in DMSO in such a fashion that the initial concentration of luminol was adjusted to be 750 μM with the addition of an aqueous solution of 1 mM hydrogen peroxide solution.

EXAMPLE 1

To the peroxidase-labelled AFP antibody prepared in Reference Example 1 was added a 0.2% BSA (bovine serum albumin) phosphate buffer solution so as to adjust the concentration of the peroxidase-labelled AFP antibody to $1.5 \times 10^{-5}$ mg/ml. 50 μl of the thus prepared dilute solution of the peroxidase-labelled AFP antibody was placed in a micro test tube. To this solution, 200 μl of any of the five reagents (a) for the assay of peroxidase activity, and then 135 μl of the luminol substrate solution (b), prepared in Reference Example 2, were added, and the mixture was allowed to stand at 37° C. for 30 minutes in a thermostat.

For comparison, a sample consisting of the peroxidase-labelled AFP antibody and the 0.2% BSA phosphate buffer solution with the concentration of the peroxidase-labelled anti-AFP being $1.5 \times 10^{-5}$ mg/ml, without addition of any reagent for the assay of peroxidase activity, was prepared, and allowed to stand at 37° C. for 30 minutes in a thermostat.

Thereafter, each sample was placed in a photoncounter (Trademark "Model 9500" made by Berthold Co., Ltd.), so that the light emission for 1 minute was measured. The quantity of the light emission for 4 seconds during a period of 10 seconds was integrated.

Table 1 shows the light emissions of the substrates of the above samples.

TABLE 1

| | Peroxidase Enhancers | Concentration | Light Emission (Counts/10 seconds) |
|---|---|---|---|
| (1) | N,N-dimethylindo-(aniline) | 1 μM | 960 |
| | | 5 | 499 |
| | | 26 | 95 |
| (2) | 2,6-dichlorophenolindo--o-cresol | 13 | 712 |
| | | 26 | 460 |
| (3) | phenolindophenol | 26 | 56.648 |
| | | 13 | 33,884 |
| (4) | N-methylphenothiazine | 50 | 38,623 |
| | | 100 | 60,714 |
| (3) | +(4) | 26 + 100 | 313,689 |
| | No addition | | 10 |

Reference Example 3

[Preparation of AFP antibody-bonded polystyrene beads]

A phosphate buffer solution (pH=7.0) was added to an AFP antibody obtained from a mouse in such a fashion that the concentration of the AFP antibody was in the range of 20 to 50 μg/ml. Sufficiently washed polystyrene beads were placed into the above solution and slowly stirred at 4° C. for 24 hours. The beads were then taken from the antibody solution and then well washed with a phosphate buffer solution (pH=7.0). The thus well washed beads were placed into a 0.2% casein solution and the blocking was performed at room temperature for 3 hours. After the termination of the blocking, the beads were again washed well with the phosphate buffer solution, whereby the AFP antibody-bonded polystyrene beads were obtained.

Reference Example 4

[Preparation of a reagent for the assay of peroxidase activity]

A mixture of N-methylphenothiazine and phenolindophenol, dissolved in DMSO, was diluted with the same buffer solution as empolyed in Reference Example 2, in such a fashion that the initial concentration of N-methylphenothiazine was 98 μM and the initial concentration of phenolindophenol was 19 μM, whereby a reagent for the assay of peroxidase activity was prepared.

EXAMPLE 2

20 μl of each of AFP standard solutions with known, but different concentrations was placed in each of 20 wells in a tray, followed by addition of 300 μl of the peroxidase-labelled AFP antibody thereto. The AFP antibody-bonded polystyrene beads, prepared in Reference Example 3, were picked up with a pincette one by one, and one bead was placed in each well. The tray was then covered with a cover seal, and the mixture in each well was well mixed by tapping the tray, and placed in a thermostat at 37° C. for 30 minutes to proceed the antigen-antibody reaction.

After the termination of the antigen-antibody reaction, the reaction liquid in each well was sucked up by an aspirator and 1 to 3 ml of a physiological saline solution was placed in each well. This physiological saline solution was then sucked up by the aspirator and removed. By repeating the step of adding the physioological saline solution to the antigen-antibody reaction mixture and removing the same therefrom by sucking three times, the bead in each well was washed and then placed in a micro test tube.

200 μl of the reagent for the assay of peroxidase activity prepared in Reference Example 4 was then placed in the micro test tube. 135 μl of the luminol substrate solution (b) prepared in Reference Example 2 was added to the above reagent in the micro test tube and allowed to react at 37° C. for 30 minutes.

The test tube containing the reaction mixture was placed in a photoncounter and the peroxidase activity was measured. The quantity of the light emission for 4 seconds during a period of 10 seconds was integrated.

FIG. 1 shows a standard curve showing the relationship between the concentration of the AFP antibody and the light emission, which was obtained by the above measurement.

EXAMPLE 3

[Measurement of Peroxidase]

A peroxidase-labelled AFP antibody (0.15 mg/ml when converted to the concentration of peroxidase) was diluted $10^{-1}$ by $10^{-1}$ with a 0.2% BSA phosphate buffer solution until the concentration reached $10^{-13}$ mg/ml. 50 μl of each dilute solution was placed in a micro test tube. 200 μl of the reagent for the assay of peroxidase activity, prepared in Reference Example 4, was added to each solution. Furthermore, 135 μl of the luminol substrate solution (b) prepared in Reference Example 2 was added thereto. The reaction mixture was allowed to stand in a thermostat at 37° C. for 30 minutes. The micro test tube containing the above reaction mixture was placed in a photoncounter and the light emission for 10 seconds was measured. The quantity of the light emission for 4 seconds during a period of 10 seconds was integrated.

Figure 2:
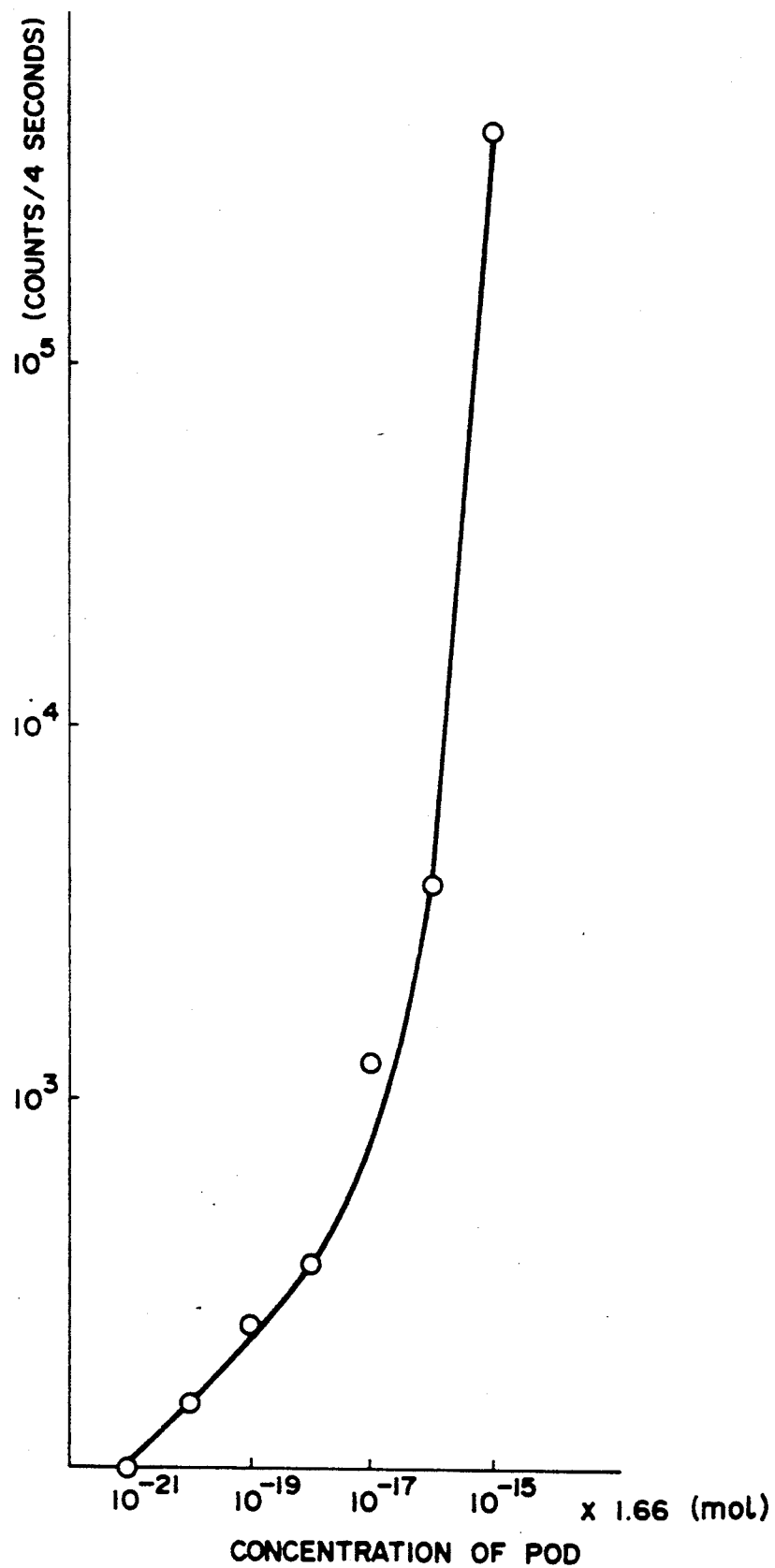
FIG. 2 shows the relationship between the concentration of the peroxidase-labelled AFP antibody and the light emission of a luminol substrate solution when a peroxidase activity enhancer comprising N-methylphenothiazine and phenolindophenol was employed.

FIG. 2 shows the relationship between the concentration of the peroxidase-labelled AFP antibody and the light emission of a luminol substrate solution when a peroxidase activity enhancer comprising N-methylphenothiazine and phenolindophenol was employed.

Reference Example 5

[Preparation of a reagent for the assay of peroxidase activity]

A solution of phenolindophenol, dissolved in DMSO, was added to a tricine-NaOH buffer solution (pH=8.4 and 50 mM) containing 0.02% Pelex OT-P in such a fashion that the initial concentration of the phenolindophenol was 43 μM, whereby a peroxidase activity enhancer comprising phenolindophenol was prepared.

EXAMPLE 4

[Measurement of Peroxidase]

Figure 3:
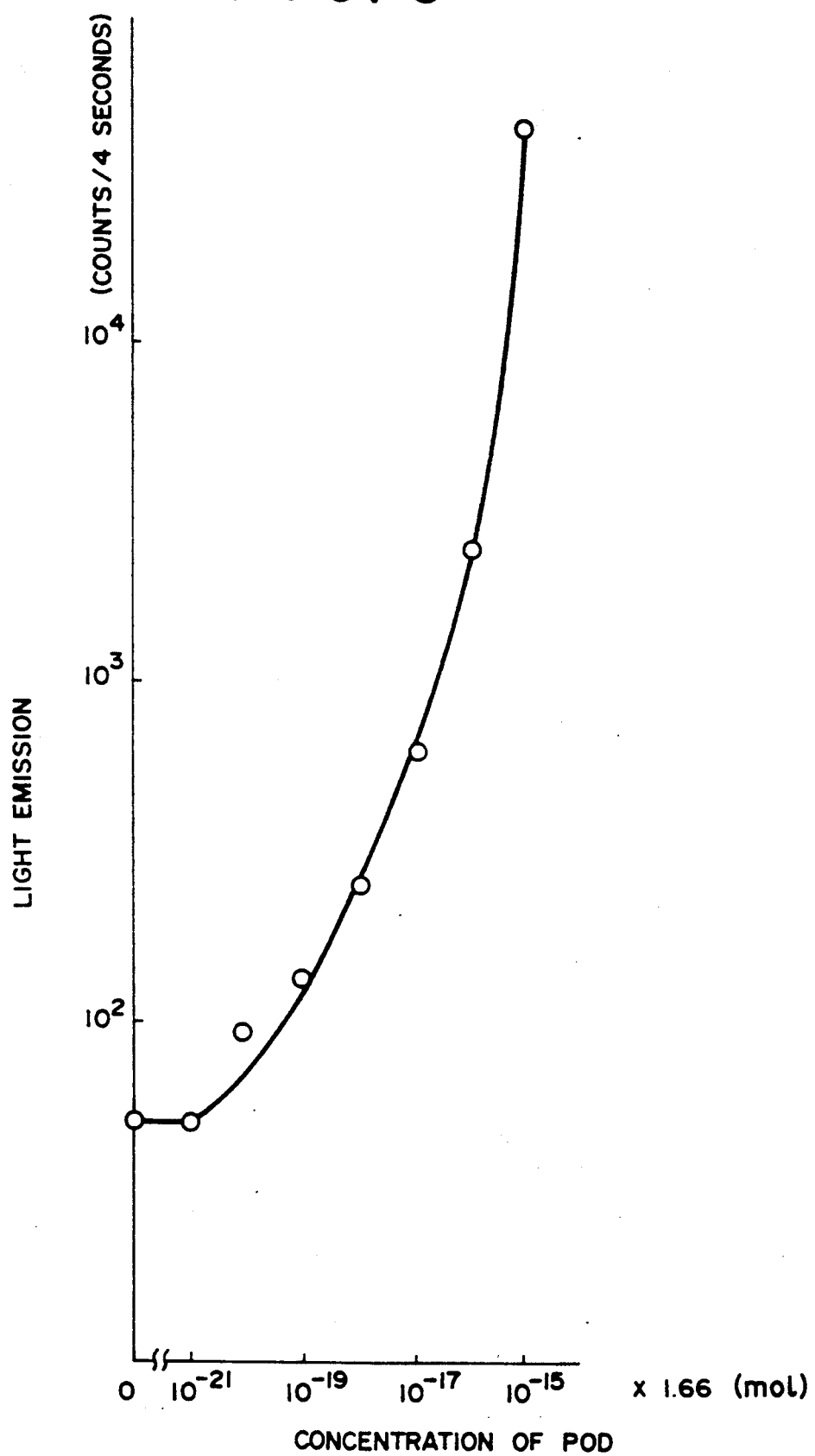
FIG. 3 shows the relationship between the concentration of the peroxidase-labelled AFP antibody and the light emission of a luminol substrate solution when a peroxidase activity enhancer comprising phenolindophenol was employed.

The procedure for Example 3 was repeated except that the reagent for the assay of peroxidase activity comprising N-methylphenothiazine and phenolindophenol employed in Example 3 was replaced by the peroxidase activity enhancer comprising phenolindophenol prepared in Reference Example 5, whereby the relationship between the concentration of the peroxidase-labelled AFP antibody and the light emission of a luminol substrate solution was investigated when the peroxidase activity enhancer comprising phenolindophenol was employed, which is shown in FIG. 3.

Reference Example 6

[Preparation of a reagent for the assay of peroxidase activity]

A solution of N-methylphenothiazine, dissolved in DMSO, was added to a tricine-NaOH buffer solution (pH=8.4 and 50 mM) containing 0.02% Pelex OT-P in such a fashion that the initial concentration of the N-methylphenothiazine was 98 μM, whereby a reagent for the assay of peroxidase activity comprising N-methylphenothiazine was prepared.

EXAMPLE 5

[Measurement of Peroxidase]

Figure 4:
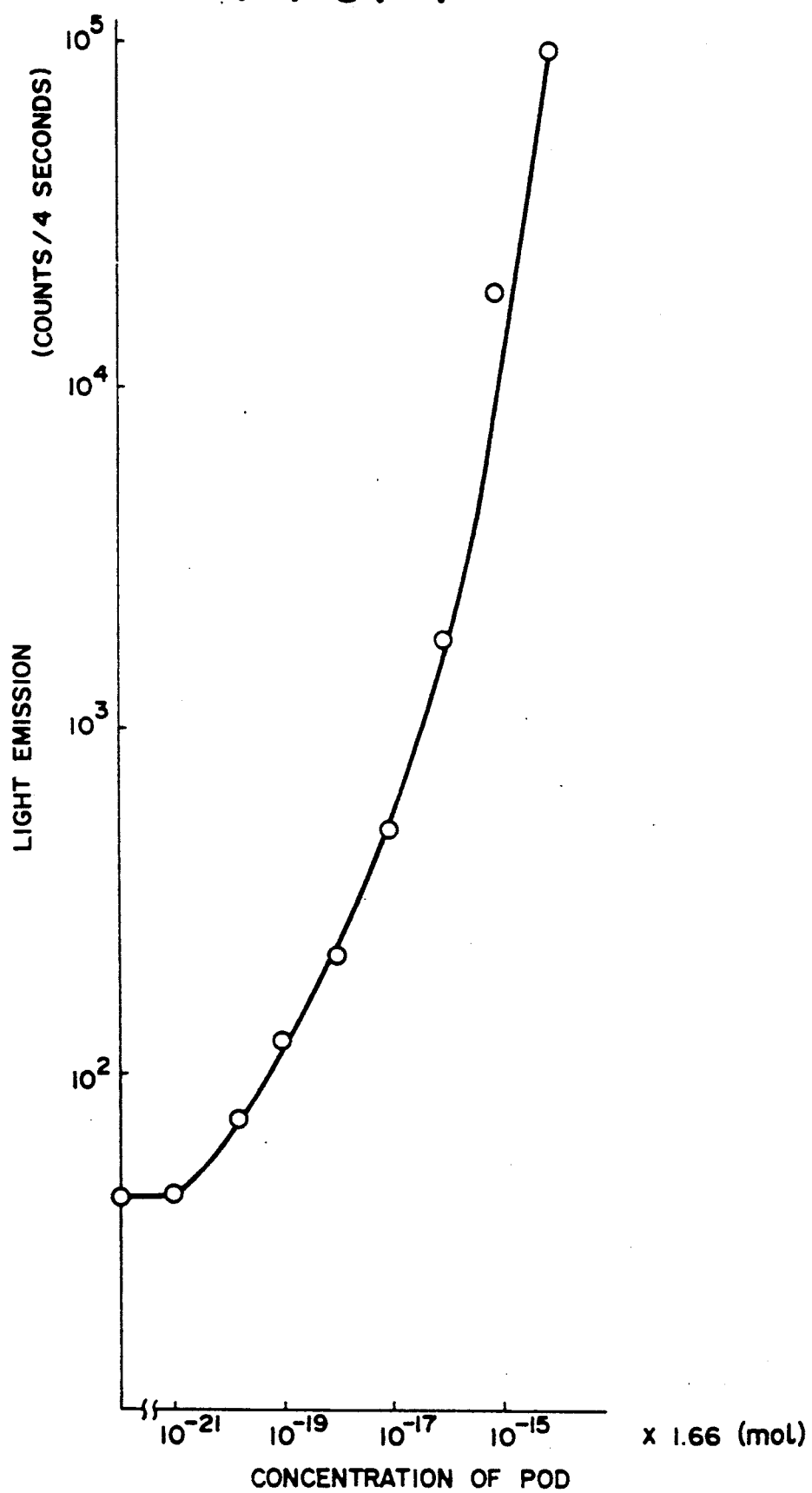
FIG. 4 shows the relationship between the concentration of the peroxidase-labelled AFP antibody and the light emission of a luminol substrate solution when a peroxidase activity enhancer comprising N-methylphenothiazine was employed.

The procedure for Example 3 was repeated except that the reagent for the assay of peroxidase activity comprising N-methylphenothiazine and phenolindophenol employed in Example 3 was replaced by the reagent for the assay of peroxidase activity comprising N-methylphenothiazine prepared in Reference Example 6, whereby the relationship between the concentration of the peroxidase-labelled AFP antibody and the light emission of a luminol substrate solution was investigated when the reagent for the assay of peroxidase activity comprising N-methylphenothiazine was employed, which is shown in FIG. 4.

Comparative Example 1

Figure 5:
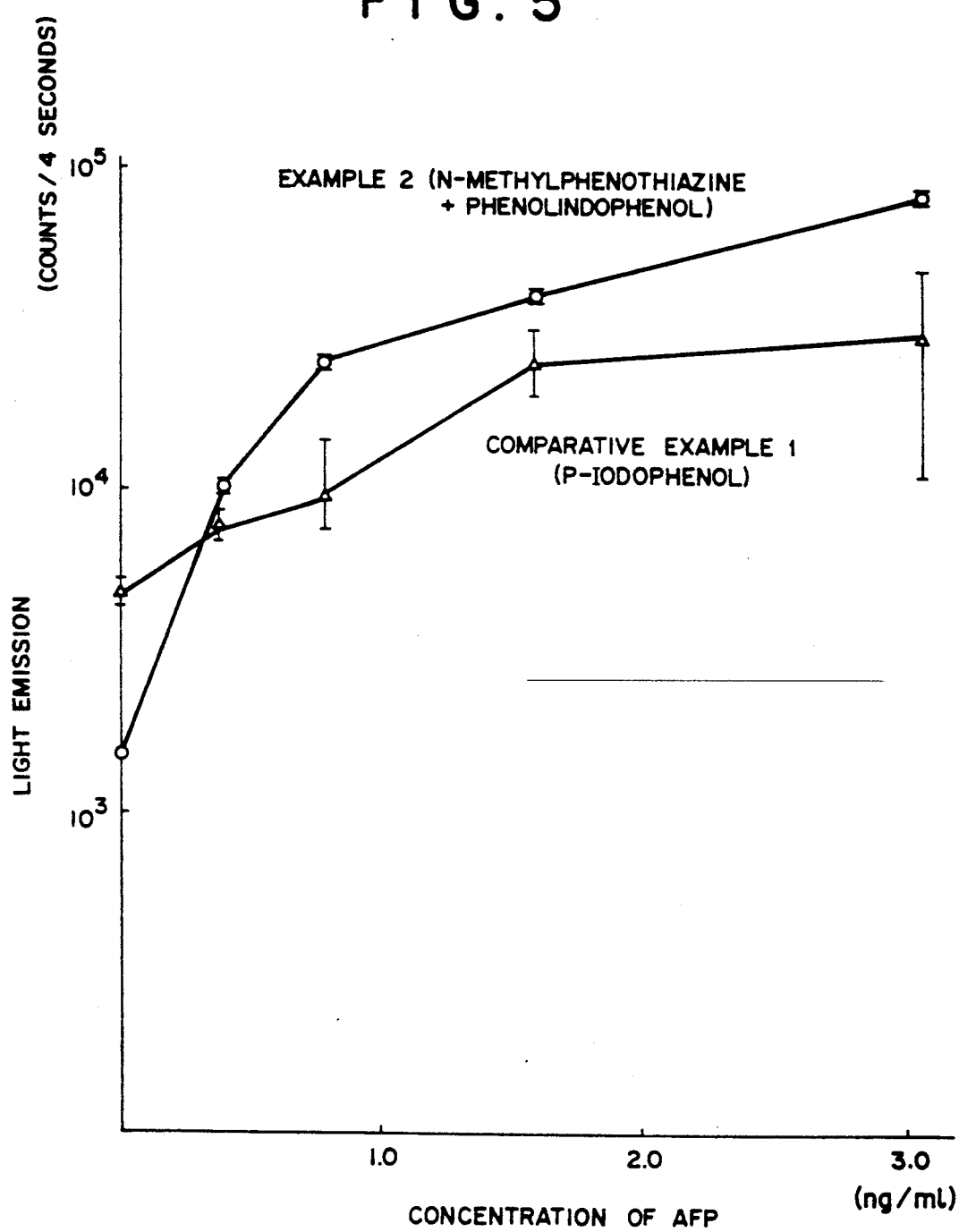
FIG. 5 shows a diagram comparing the light emission by the method described in Example 2 and that in a conventional chemiluminescence method in which p-iodophenol was used as a peroxidase activity enhancer.

The procedure for Example 2 was repeated except that the peroxidase activity enhancer in the reagent for the assay of peroxidase activity employed in Example 2 was replaced by p-iodophenol. The result is shown in FIG. 5.

Reference Example 7

[Preparation of peroxidase-labelled tyroid-stimulating hormone antibody (TSH antibody)]

A TSH antibody was obtained from a mouse and subjected to pepsin digestion, so that F(ab')$_2$ was obtained in accordance with a conventional method as described in "Enzyme Immuno Assay" 3rd Edition, page 86-, published by Igaku-shoin Co., Ltd.

1 ml of the thus obtained TSH antibody was dialyzed against a 0.1M phosphate buffer solution (pH=6.3, containing 1 mM EDTA. 50 μl of 0.2M 2-mercaptoethylamine was added to this mixture and then allowed to stand at 37° C. for 3 hours, followed by desalting by use of G-25, whereby Fab' was obtained.

To a peroxidase solution with a concentration of 20 mg/ml, dissolved in a 0.1M phosphonate buffer solution (pH=7.0), there was added a dimethlformamide (DMF) solution of succimidyl-4-(N-maleinimidomethyl)cyclohexane-1-carboxylate (SMCC)(10 mg/150 μl), and the mixture was allowed to react with stirring at 30° C.

The reaction mixture was then centrifuged so that a precipitate formed therein was removed therefrom. The reaction mixture was desalted by use of G-25 in the same manner as mentioned above.

The previously obtained Fab' and the MMC peroxidase was mixed in a molar ratio of 1:2 and then allowed to react at 4° C. for 24 hours, followed by purifying the reaction product with gel chromatography, whereby a peroxidase-labelled TSH was obtained.

Reference Example 8

[Preparation of a reagent for the assay of peroxidase activity]

A solution of phenothiazine-10-yl-propylsulfonate and phenolindophenol was prepared in such a fashion that the concentration of phenothiazine-10-yl-propylsulfonate was 1.0 mM and the concentration of phenolindophenol was 0.1 mM with addition of a tricine-NaOH buffer solution (pH=8.4 and 4.50 mM), whereby a reagent for the assay of peroxidase activity was prepared.

Reference Example 9

[Preparation of TSH antibody-bonded polystyrene beads]

A phosphate buffer solution (pH=7.0) was added to an TSH antibody obtained from a mouse in such a fashion that the concentration of the TSH antibody was in the range of 20 to 50 μg/ml. Sufficiently washed polystyrene beads were placed into the above solution and slowly stirred at 4° C. for 24 hours. The beads were then taken from the antibody solution and then well washed with a phosphate buffer solution (pH=7.0). The thus well washed beads were placed into a 0.2% casein solution and the blocking was performed at room temperature for 3 hours. After the termination of the blocking, the beads were again washed well with the phosphate buffer solution, whereby the TSH antibody-bonded polystyrene beads were obtained.

EXAMPLE 6

20 μl of each of TSH standard solutions with known, but different concentrations was placed in each of 20 wells in a tray, followed by addition of 300 μl of the peroxidase-labelled TSH antibody thereto. The TSH antibody-bonded polystyrene beads, prepared in Reference Example 9, were picked up with a pincette one by one, and one bead was placed in each well. The tray was then covered with a cover seal, and the mixture in each well was well mixed by tapping the tray, and placed in a thermostat at 37° C. for 30 minutes to proceed the antigen-antibody reaction.

After the termination of the antigen-antibody reaction, the reaction liquid in each well was sucked up by an aspirator and 1 to 3 ml of a physiological saline solution was placed in each well. This physiological saline solution was then sucked up by the aspirator and removed. By repeating the step of adding the physiological saline solution to the antigen-antibody reaction mixture and removing the same therefrom by sucking three times, the bead in each well was washed and then placed in a micro test tube.

200 μl of the reagent for the assay of peroxidase activity prepared in Reference Example 8 was then placed in the micro test tube. 135 μl of the luminol substrate solution (b) prepared in Reference Example 2 was added to the above reagent in the micro test tube and allowed to react at 37° C. for 30 minutes.

The test tube containing the reaction mixture was placed in a photoncounter and the peroxidase activity was measured. The quantity of the light emission for 4 seconds during a period of 10 seconds was integrated.

Figure 6:
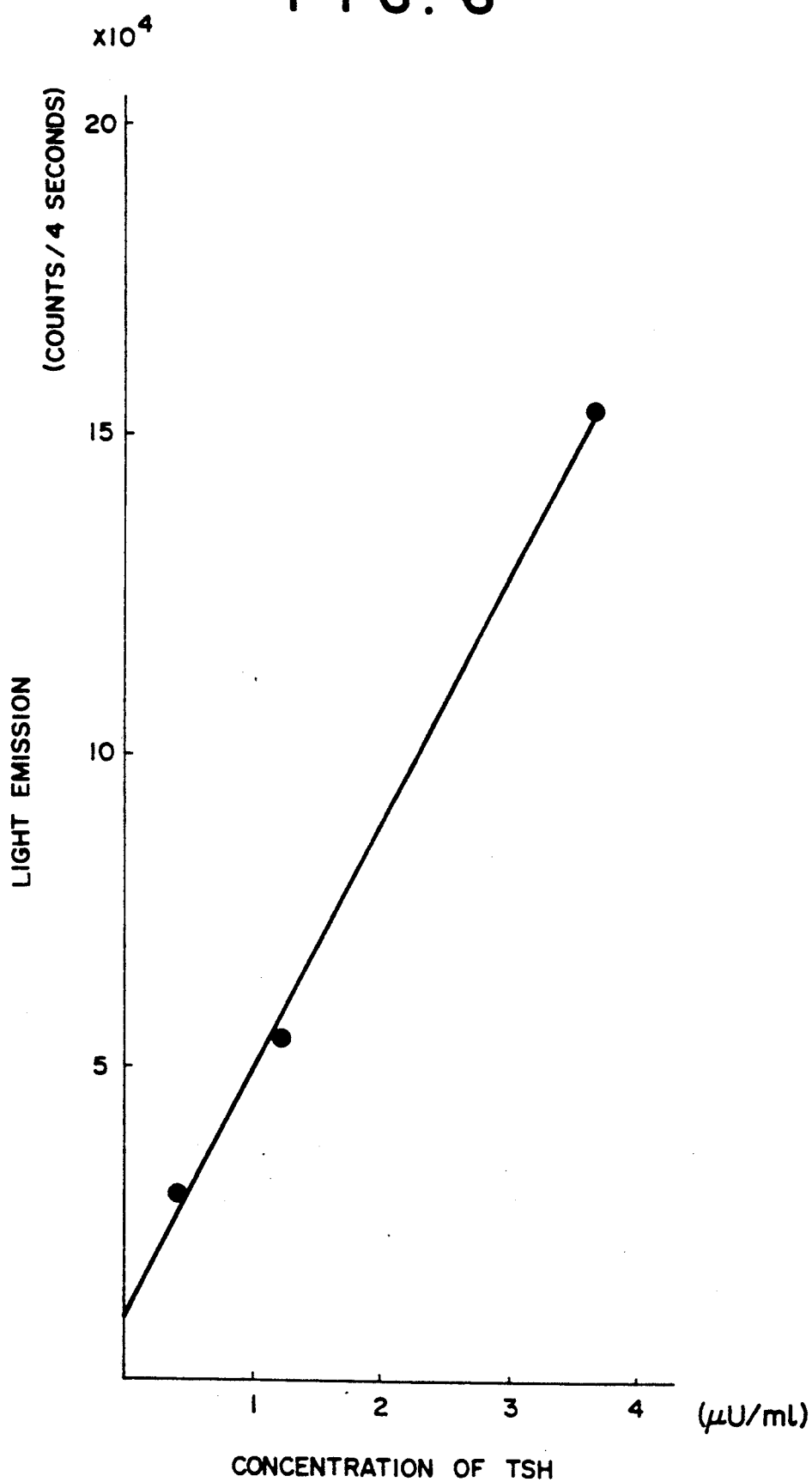
FIG. 6 shows a standard curve showing the relationship between the concentration of TSH and the light emission thereof obtained in Example 6.

FIG. 6 shows a standard curve showing the relationship between the concentration of the TSH antibody and the light emission, which was obtained by the above measurement.

Figure 7:
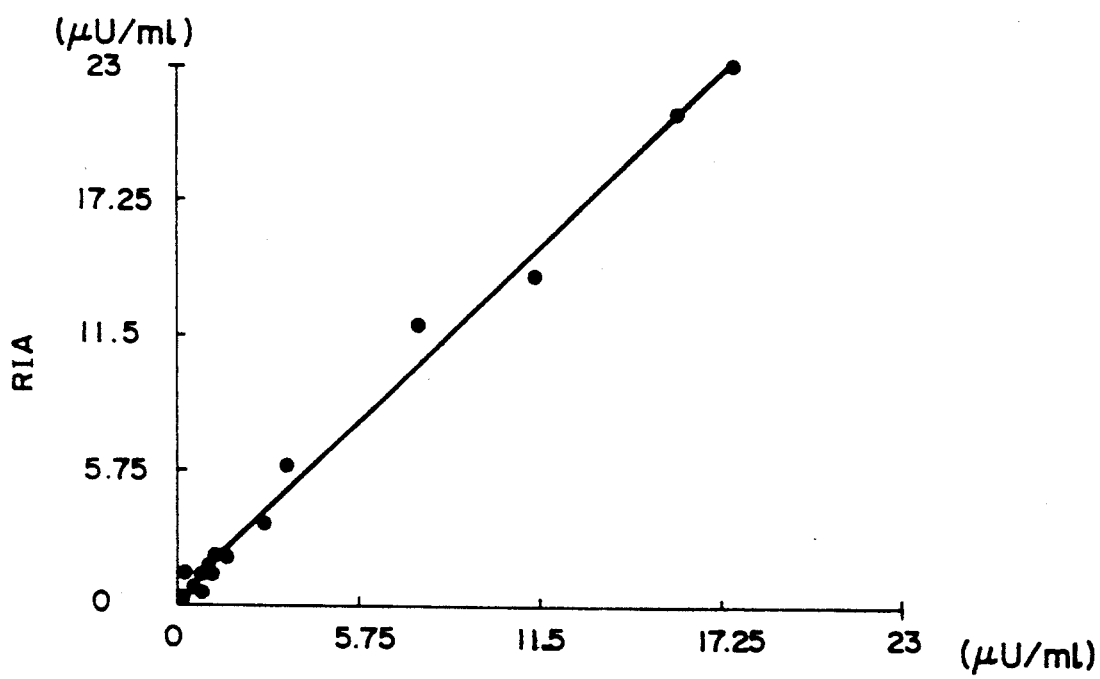
FIG. 7 shows the correlation between the TSH values obtained by the method described in Example 6 and the TSH values obtained by RIA.

The above procedure was exactly repeated using 17 serum samples and the relationship between the TSH concentration (μU/ml) and the light emission (counts/4 seconds) was obtained. Furthermore, the above relationship was also obtained by radioimmunoassay (RIA) and the correlation between the TSH values obtained by the above method according to the present invention and the TSH values obtained by RIA was obtained as shown in FIG. 7. The results shown in FIG. 7 indicate that there is an excellent correspondence between the two methods.

Reference Example 10

[Preparation of a reagent for the assay of peroxidase activity]

A solution of phenothiazine-10-yl-propylsulfonate and phenolindophenol was prepared in such a fashion that the concentration of phenothiazine-10-yl-propylsulfonate was 0.2 mM and the concentration of phenolindophenol was 0.1 mM with addition of a tricine-NaOH buffer solution (pH=8.4 and 4.50 mM), whereby a reagent for the assay of peroxidase activity was prepared.

EXAMPLE 7

20 μl of each of TSH standard solutions with known, but different concentrations was placed in each of 20 wells in a tray, followed by addition of 300 μl of the peroxidase-labelled TSH antibody thereto. The TSH antibody-bonded polystyrene beads, prepared in Reference Example 3, were picked up with a pincette one by one, and one bead was placed in each well. The tray was then covered with a cover seal, and the mixture in each well was well mixed by tapping the tray, and placed in a thermostat at 37° C. for 30 minutes to proceed the antigen-antibody reaction.

After the termination of the antigen-antibody reaction, the reaction liquid in each well was sucked up by an aspirator and 1 to 3 ml of a physiological saline solution was placed in each well. This physiological saline solution was then sucked up by the aspirator and removed. By repeating the step of adding the physioological saline solution to the antigen-antibody reaction mixture and removing the same therefrom by sucking three times, the bead in each well was washed and then placed in a micro test tube.

200 μl of the reagent for the assay of peroxidase activity prepared in Reference Example 10 was then placed in the micro test tube. 135 μl of the luminol substrate solution (b) prepared in Reference Example 2 was added to the above reagent in the micro test tube and allowed to react at 37° C. for 30 minutes.

The test tube containing the reaction mixture was placed in a photoncounter and the peroxidase activity was measured. The quantity of the light emission for 4 seconds during a period of 10 seconds was integrated.

Figure 8:
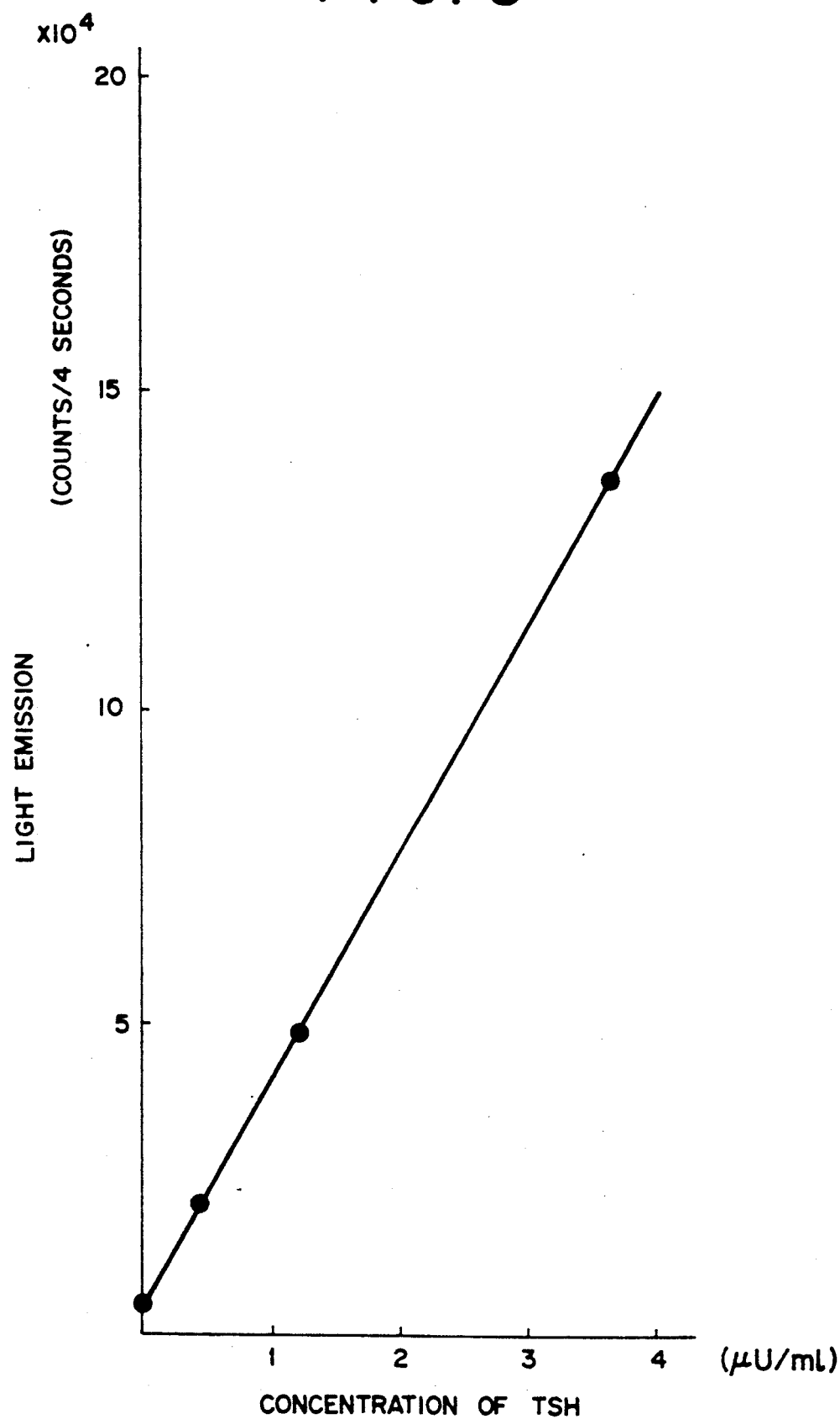
FIG. 8 shows a standard curve showing the relationship between the concentration of TSH antibody and the light emission thereof obtained in Example 7.

FIG. 8 shows a standard curve showing the relationship between the concentration of the TSH and the light emission, which was obtained by the above measurement.

Figure 9:
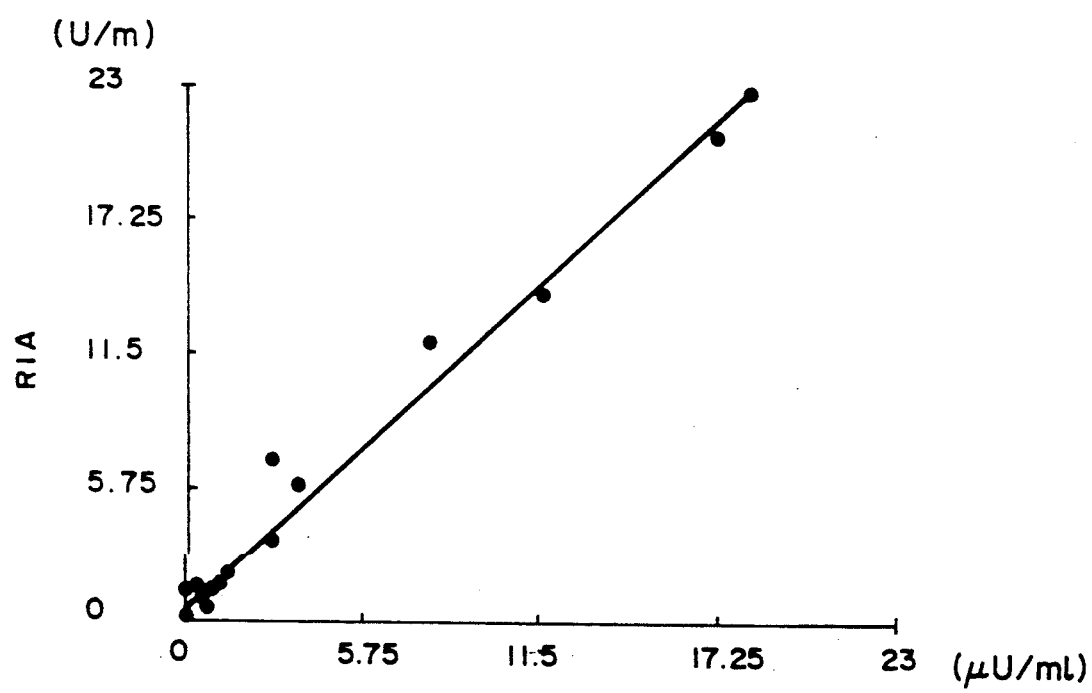
FIG. 9 shows the relationship between the TSH values obtained by the method described in Example 7 and the TSH values obtained by RIA.

The above procedure was exactly repeated using 17 serum samples and the relationship between the TSH concentration (μU/ml) and the light emission (counts/4 seconds) was obtained. Furthermore, the above relationship was also obtained by radioimmunoassay (RIA) and the correlation between the TSH values obtained by the above method according to the present invention and the TSH values obtained by RIA was obtained as shown in FIG. 9. The results shown in FIG. 9 indicate that there is an excellent correspondence between the two methods.

The method of the chemiluinescence assay of the activity of peroxidase according to the present invention is capable of attaining higher assay performance than the conventional colorimetric method using ABTS having high coloring sensitivity. More specifically, the assay performance of the present invention is 300 to 750 times that of the colorimetric method in terms of S/N ratio, and about 1000 times in terms of detection sensitivity. Furthermore, the present invention can detect the activity of peroxidase with high reproducibility even if the concentration of peroxidase is at such a low concentration that cannot be detected by a conventional method of the chemiluminescence assay of the activity of peroxidase using p-iodophenol, which has been considered to attain the highest detection sensitivity.

What is claimed is:

1. A method of chemiluminescent assay of the activity of peroxidase, which comprises:
   reacting a peroxidase-labeled antibody with antigen to form an antigen-antibody complex;
   allowing said antigen-antibody complex to react with a fixed antibody;
   combining a luminol or isoluminol substrate, hydrogen peroxide and an assay reagent of at least one compound, which serves as a peroxidase activity enhancer selected from the group consisting of N,N-dimethylindo-(aniline), 2,6-dichlorophenolindo-o-cresol, phenolindophenol, N-methylphenothiazine and mixtures thereof, with the labeled antigen-antibody reaction product, thereby performing a chemiluminescent reaction and measuring the quantity of light emitted from said reaction.

2. The method of claim 1, wherein said activity enhancer comprises phenolindophenol and N-methylphenothiazine.

3. The method of claim 1, wherein said activity enhancer comprises phenolindophenol and sodium phenothiazine-10-yl-propylsulfonate.

* * * * *

UNITED STATES PATENT AND TRADEMARK OFFICE
CERTIFICATE OF CORRECTION

PATENT NO. : 5,171,668

DATED : December 15, 1992

INVENTOR(S) : Masami SUGIYAMA, et al

It is certified that error appears in the above-identified patent and that said Letters Patent is hereby corrected as shown below:

Title Page:
Abstract, line 4, "at lease one compound," should read --at least one compound--.

Column 1, line 31, "using as p-iodophenol" should read --using a p-iodophenol--.

Column 2, line 57, "of TSH antibody and" should read --of TSH and--.

Column 3, line 24, "2,6-dichlorophenol-o-cresol," should read --2,6-dichlorophenolindo-o-cresol,--.

Column 8, line 61, "3-chloropyrimdiylphenothiazine-10" should read --3-chloropyrimidylphenothiazine-10--.

Column 10, line 38, "3-chlorodiyrazinophenoxazine" should read --3-chlorodipyrazinophenoxazine--.

Column 11, line 60, "antigens such HBs," should read --antigens such as HBs,--.

Column 12, line 2, "referring the following" should read --referring to the following--.

Column 12, line 23, "a dimethlformamide" should read --a dimethylformamide--.

Column 13, line 28, "313,689" should read --213,689--.

UNITED STATES PATENT AND TRADEMARK OFFICE
CERTIFICATE OF CORRECTION

PATENT NO. : 5,171,668
DATED : December 15, 1992
INVENTOR(S) : Masami SUGIYAMA, et al It is certified that error appears in the above-identified patent and that said Letters Patent is hereby corrected as shown below:

Column 14, line 13, "the physioological saline" should read --the physiological saline--.

Column 15, line 51, "tyroid-stimulating" should read --thyroid-stimulating--.

Column 15, line 66, "dimethlformamide" should read --dimethylformamide--.

Column 17, line 10, "TSH antibody and" should read --TSH and--.

Column 17, line 55, "the physioological" should read --the physiological--.

Signed and Sealed this

First Day of February, 1994

Attest:

BRUCE LEHMAN

Attesting Officer    Commissioner of Patents and Trademarks